United States Patent [19]

Bark et al.

[11] Patent Number: 5,074,878
[45] Date of Patent: Dec. 24, 1991

[54] TISSUE EXPANDER AND METHOD

[75] Inventors: Jeffrey E. Bark, Racine; Jeffrey R. Gengler, Milwaukee; William Hubbard, East Troy; Donald V. Hillegass, Franksville; Eric J. Woodruff, Racine, all of Wis.

[73] Assignee: Medical Engineering Corporation, Racine, Wis.

[21] Appl. No.: 688,367

[22] Filed: Apr. 19, 1991

Related U.S. Application Data

[63] Continuation of Ser. No. 343,329, Apr. 24, 1989, abandoned, which is a continuation of Ser. No. 62,305, Jun. 12, 1987, abandoned.

[51] Int. Cl.$^5$ .............................................. A61F 2/12
[52] U.S. Cl. ............................................ 623/8; 623/11
[58] Field of Search ............................ 623/7, 8, 11, 12

[56] References Cited

U.S. PATENT DOCUMENTS

| | | | |
|---|---|---|---|
| 3,559,214 | 2/1975 | Pangman | 623/8 |
| 3,640,269 | 2/1972 | Delgado | 604/93 |
| 4,019,499 | 4/1977 | Fitzgerald | 128/1 R |
| 4,205,401 | 6/1980 | Frisch | 623/8 |
| 4,413,359 | 11/1983 | Akiyama | 128/DIG. 14 |
| 4,428,364 | 1/1984 | Bartolo | 128/1 R |
| 4,459,167 | 7/1984 | Markow et al. | 156/110.5 |
| 4,685,447 | 8/1987 | Iversen et al. | 623/8 |

Primary Examiner—David J. Isabella
Attorney, Agent, or Firm—Stuart E. Krieger

[57] ABSTRACT

The tissue expander includes a closed shell structure having a shell wall formed of a needle-penetrable material with self-sealing characteristics. The shell defines a fluid expandable chamber. In some embodiments of the invention, a self-sealing layer of elastomeric material is joined or otherwise bonded to an inner surface of a non-flowable layer of elastomeric material. In other embodiments of the invention, the self-sealing layer is joined to the outer surface of a layer of non-flowable elastomeric material. The self-sealing layer may also be sandwiched between two layers of non-flowable elastomeric material. In a further embodiment the self-sealing layer constitutes the entire shell of the tissue expander. In all embodiments of the invention, a needle stop member is provided to prevent a needle that accesses the fluid chamber from passing outwardly of the tissue expander in the same direction in which it has accessed the fluid chamber. Fluid for expanding the chamber is infused directly therein through a needle that penetrates the shell wall. The self-sealing material seals any opening in the shell wall produced by removal of the infusion needle. Self-sealing is accomplished by a flowing together of wall material at the needle opening when the needle is withdrawn from the wall.

20 Claims, 3 Drawing Sheets

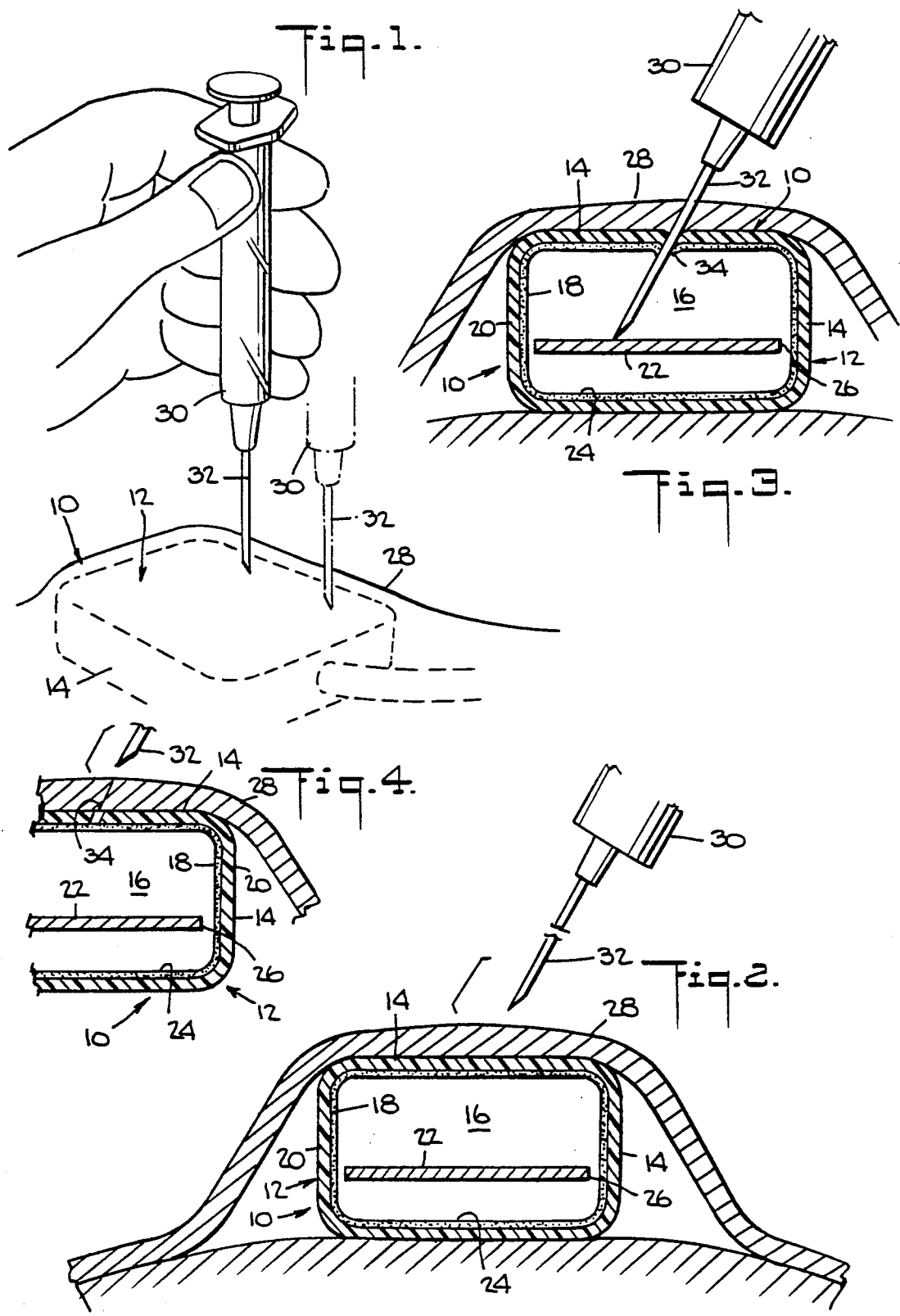

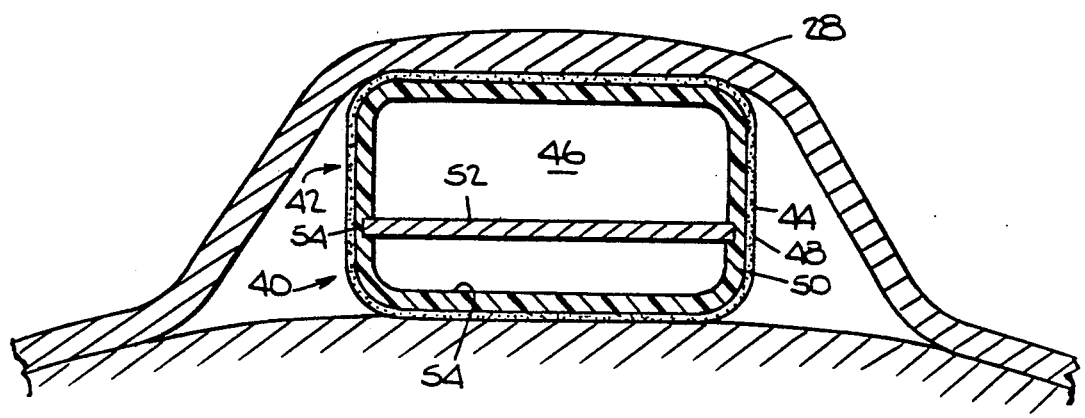
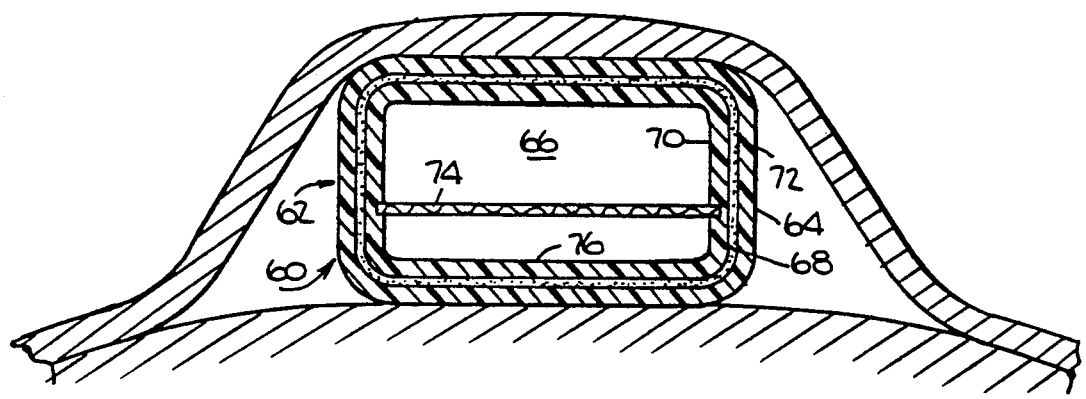
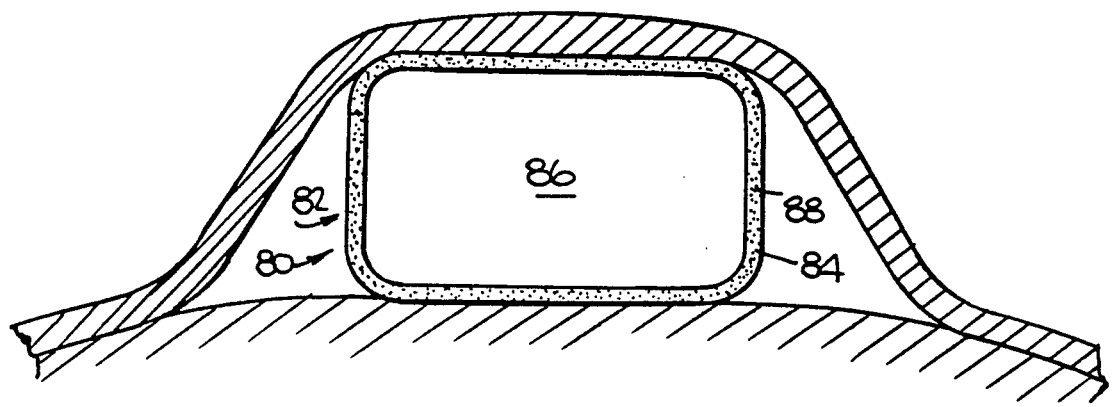

TISSUE EXPANDER AND METHOD

This is a continuation of application Ser. No. 343,329, filed Apr. 24, 1989, now abandoned, which is a continuation of application Ser. No. 062,305, filed Jun. 12, 1985, now abandoned.

BACKGROUND OF THE INVENTION

This invention relates to implantable devices for promoting tissue growth or tissue expansion, and more particularly to a fluid expandable prosthetic device that does not require a valving arrangement for the infusion or removal of fluid.

Tissue expansion devices have long been used to produce a flap of skin for covering or accommodating a prosthetic device. The skin flap is usually formed at or adjacent to a designated area that has been structurally deformed or superficially altered due to illness, accident or surgery, for example.

The process of tissue expansion often begins by subcutaneously implanting a tissue expander, in a contracted condition, at a selected location. The tissue expander is gradually enlarged by the infusion of fluid into a fluid chamber of the expander.

The infusion process is usually accomplished through a fluid inlet valve arrangement that is directly or indirectly connected to the tissue expander chamber. For example, U.S. Pat. No. 4,190,040 discloses a tissue expansion device with a resealable fluid inlet valve that is connected to the expansion device via a connection tube.

The term "valve arrangement" as used herein is intended to refer to a predetermined path of fluid flow from a fluid inlet valve into a tissue expander chamber through an entry port of the chamber, and also contemplates a fluid flow conduit connecting the entry port to the fluid inlet valve. The term "entry port" as used herein refers to a predetermined fluid inlet opening in a tissue expander chamber and also contemplates an opening defined by a fluid inlet valve.

Other tissue expansion devices, such as shown in U.S. Pat. Nos. 4,217,889 and 4,643,733 include valving arrangements that are connected directly or indirectly to the expansion chamber by means of a tube or other similar passageway.

Tissue expanders with valve arrangements normally require surgical implantation of the tissue expander portion of the device, the fluid inlet valve and any connection tube that joins the valve to the expansion chamber. The extensiveness of the implant surgery thus corresponds to the size and extent of the tissue expander and its accompanying valve arrangement and conduit.

Ordinarily, the access portion of a fluid inlet valve is of substantially less size than the tissue expansion chamber, and represents a relatively small target area in which to insert a needle for infusing or withdrawing fluid. Since repetitive infusions are usually required to accomplish a desired tissue expansion, the skin in the area of the infusion valve often becomes sensitized due to frequent penetrations by an infusion needle in a predetermined small area.

A further problem inherent in the use of tissue expansion devices that have valve arrangements connected to the tissue expansion chamber is the surgical scope of a removal operation when the tissue expansion device is to be withdrawn. The removal operation requires an incision that is large enough to extract both the tissue expansion chamber and the valve arrangement, and is generally of similar extent to the surgery used in installing the tissue expansion device and valve arrangement.

It is thus desirable to provide a tissue expansion device which does not require a valve arrangement for the intake or removal of fluid, and which can be installed with a relatively small surgical incision.

OBJECTS AND SUMMARY OF THE INVENTION

Among the several objects of the invention may be noted the provision of a novel tissue expander, a novel tissue expander with a self-sealing expansion chamber, a novel tissue expander having an expansion chamber in which fluid can be infused or removed without a valve arrangement, a novel tissue expander which can be infused with fluid over a relatively large peripheral section of the expansion chamber, a tissue expander with more than one expansion chamber, a tissue expander with a plurality of non-communicable expansion chambers that are self-sealing, and a novel method of expanding tissue.

Other objects and features of the invention will be in part apparent and in part pointed out hereinafter.

In accordance with the present invention, the tissue expander includes a closed shell having a wall formed of a needle-penetrable material. The shell wall, which defines an expandable internal chamber, includes a layer of self-sealing elastomeric material.

The shell is substantially collapsible when empty, thereby facilitating implantation. Following implantation, the shell is gradually expanded to a predetermined size and shape by periodic infusions of fluid into the chamber using a needle to directly penetrate the shell wall.

When infusion is completed, the needle is withdrawn from the shell. The opening or needle hole in the shell wall left by the needle when it is removed is sealed by the self-sealing layer. Sealing results from a flowing together of wall material at the opening when the needle is withdrawn from the shell wall.

The tissue expander has no valve arrangement to permit communication with the chamber, nor is there any entry port into the chamber. Any infusion of fluid into the chamber is accomplished by means of a syringe penetrating the tissue expander wall. Removal of fluid from the tissue expander chamber also requires penetration of the shell wall by a needle, which withdraws fluid from the chamber.

The tissue expander can also includes a needle stop member for preventing a syringe needle from passing directly out of the tissue expander chamber once it has accessed the chamber.

In several embodiments of the invention, a self-sealing layer of elastomeric material is bonded or otherwise joined to a layer of non-flowable elastomeric material. The self-sealing layer can be bonded to an interior or exterior surface of the non-flowable material.

In another embodiment of the invention, the self-sealing material is sandwiched between the two layers of non-flowable material.

In an further embodiment of the invention, the self-sealing layer constitutes the entire shell wall of the tissue expander.

In still another embodiment of the invention, the tissue expander includes a plurality of separate internal chambers which are noncommunicable with each other. Each of the chambers must be separately infused with fluid and require separate depletion of fluid when fluid removal is desired. The separate internal chambers may be divided by a common wall or a plurality of shells can be connected in spaced relationship.

A further embodiment of the invention includes flexible mesh material incorporated in the shell wall to control expansion of the expander chamber and/or improve the self-sealing characteristics of the self-sealing layer.

Tissue expansion is thus accomplished by forming a collapsible closed shell with a wall of needle-penetrable material. The wall of the shell is rendered self-sealing with respect to needle penetration by use of a material that flows together at a needle opening in the wall when the needle is inserted into and withdrawn from the wall. The self-sealing material is provided throughout substantially the entire area of the shell, and the space within the shell is devoid of any valve arrangement such that any introduction of fluid into the shell or removal of fluid from the shell is accomplished by penetration of the shell wall with a needle.

The invention accordingly comprises the constructions and method hereinafter described, the scope of the invention being indicated in the claims.

DESCRIPTION OF THE DRAWINGS

In the accompanying drawings,

FIG. 1 is a simplified perspective view of a tissue expander incorporating one embodiment of the invention;

FIG. 2 is a sectional view thereof prior to fluid infusion;

FIG. 3 is a sectional view thereof during fluid infusion;

FIG. 4 is a sectional view thereof after fluid infusion has taken place;

FIGS. 5-10 are sectional views of further embodiments of the invention.

Corresponding reference characters indicate corresponding parts throughout the several views of the drawings.

DETAILED DESCRIPTION OF THE INVENTION

Figure 8:
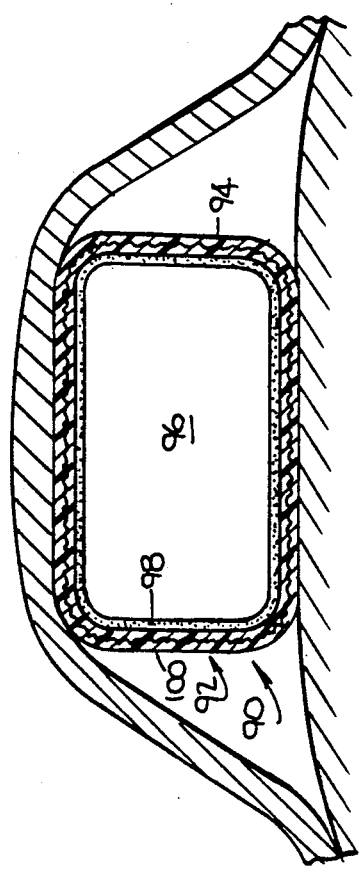

A tissue expander incorporating one embodiment of the invention is generally indicated by the reference number 10 in FIG. 1.

Referring to FIGS. 2-4, the tissue expander 10 comprises a closed shell 12 formed with a shell wall 14 that defines an expandable internal chamber 16.

The wall 14 includes a self-sealing layer or shell 18 of elastomeric material such bromo-butyl rubber, latex rubber, silicone gel, hydrogel compound or other suitable biocompatible compound which will flow or swell to seal a small opening caused by a needle penetration.

The self-sealing layer 18 is bonded or otherwise joined to a layer or shell 20 of non-flowable elastomeric material such as silicone rubber, polyurethane elastomer, polyester or other suitable known biocompatible material.

A needle stop member 22 which is substantially coextensive with a base portion 24 of the shell 12 is disposed in a free-float arrangement in the chamber 16. The needle stop member 22 is in the form of a solid sheet or mesh, and is preferably made of stainless steel. The size and arrangement of the needle stop member 22 are selected to prevent flipover of the needle stop member 22.

If desired, the needle stop member 22 can be attached around its peripheral edge 26 to the wall 14 in any suitable known manner. The attachment can be made over any pre-selected peripheral extent of the edge 26.

The base 24 may have a relatively stiff fabric or plate (not shown) embedded therein to allow uniform distribution of underlying forces against the base. Other embodiments of the invention can also include a similarly embedded fabric or plate in the base.

In using the tissue expander 10, an implantation thereof is made under the skin 28 at a pre-selected area. The tissue expander 10 is in a contracted or collapsed condition (not shown) when implanted and is thus easily accommodated under the skin 28.

Tissue expansion results from periodic infusions of fluid, such as saline liquid, into the chamber 16 over a predetermined period of time. For example, an initial infusion can be accomplished with a syringe 30, to infuse a first predetermined amount of liquid into the chamber 16. The amount of liquid infused is not intended to expand the chamber 16 to full capacity since tissue expansion is best achieved as a gradual process.

It should be noted that the tissue expander 10 does not include a valve arrangement and the chamber 16 is not provided with a fluid infusion entry port.

When the syringe 30 is directed towards the tissue expander 10 a needle 32 penetrates the skin 28 as well as the shell wall 14 to obtain access to the chamber 16. The needle stop member 22 prevents movement of the syringe needle 32 out of the chamber 16 while the needle 32 is accessing the tissue expander 10.

When an infusion of fluid has been completed, the needle 32 is withdrawn from the shell wall 14 and the skin 28, resulting in the formation of a small needle opening 34 in the self-sealing layer 18 and the non-flowable layer 20. However, the self-sealing layer 18 will flow or expand into the opening 34 left by the needle when it is withdrawn from the tissue expander 10.

As a result, the opening 34 in the self-sealing layer will be filled or otherwise closed by the material which constitutes the self-sealing layer 18. In addition, the self-sealing layer 18 will flow into the opening 34 formed in the non-flowable layer 20 thereby filling, plugging or otherwise closing the opening 34.

When additional fluid is required in the tissue expander 10 the syringe needle 32 is again directed toward the chamber 16, as previously described, for infusion of a predetermined amount of liquid therein. It will be appreciated that wherever the syringe needle 32 penetrates the shell wall 14 to access the chamber 16, said needle will pass through the self-sealing layer 18, since the layer 18 encompasses the entire chamber 16. Thus, wherever the needle 32 is withdrawn from the chamber 16, the self-sealing layer 18 will seal the hole or opening 34 that is formed when the needle 32 is withdrawn.

In similar fashion, when fluid must be withdrawn from the chamber 16, the needle 32 is directed into the chamber 16, and a desired amount of fluid is drawn from the chamber 16 into the syringe 30. Withdrawal of the needle 32 from the tissue expander again results in the formation of the opening 34 in the self-sealing layer 18 and the non-flowable layer 20. The opening 34 in the self-sealing layer 18 and in the non-flowable layer 20 is sealed in a manner similar to that previously described.

Although the tissue expander 10 is shown with a generally rectangular cross section, it can be formed to expand to any predetermined shape or size.

As shown in dotted outline in FIG. 1, repeated infusions of liquid into the tissue expander 10 can be accomplished through any accessible location on the shell wall 14 of the tissue expander 10. Thus, there is no need to make numerous needle penetrations in a small section of skin since substantially the entire skin area that covers the tissue expander 10 can be penetrated. The likelihood of sensitizing the skin which covers the tissue expander is thus minimized.

Although the precise dimensions of the tissue expander 10 may vary in accordance with the intended use, to exemplify the magnitudes being dealt with, the self-sealing layer 18 can be 0.2 millimeters thick, the non-sealing layer 20 can be 0.2 millimeters thick. The self-sealing layer is preferably formed of bromobutyl rubber or methyl vinyl siloxane.

It should be noted that in the contracted condition of the tissue expander 10, the self-sealing layer 18 might stick to itself and prevent fluid expansion of the tissue expander chamber 16. This problem can be dealt with by using a hydrophylic coating such as dimethyl siloxane or by using a very fine biocompatible powder such as hydroxylapatite. This approach can be used with all embodiments of the invention.

Another embodiment of the tissue expander is generally indicated by the reference number 40 in FIG. 5. The tissue expander 40 comprises a closed shell 42 formed with a wall 44 that defines an expandable internal chamber 46.

The wall 44 includes a self-sealing layer or shell 48 of elastomeric material, identical to that described for the shell 18, bonded or otherwise joined to the outside of a layer or shell 50 of non-flowable elastomeric material identical to that of the layer 20.

The tissue expander 40 also includes a needle stop member 52 similar to the needle stop member 22. However the needle stop member 52 is peripherally attached to the wall 44 at the layer 50, along a predetermined peripheral extent of an edge 54 of the needle stop member 52.

The tissue expander 40 is used in a manner similar to that described for the tissue expander 10 and has no valve arrangement or entry port. For example, the syringe 30 (FIG. 1) is used to infuse the chamber 46 and will cause an opening such as 34 (FIGS. 3 and 4) in the non-sealing layer 50 when the syringe needle 32 is withdrawn. However, the self-sealing layer 48 will swell, flow or otherwise expand into the opening 34 left by withdrawal of the needle 32, thereby plugging or closing such opening.

Communication between the portions of the chamber 16 above and below the needle stop member 52 is accomplished by provision of small openings (not shown) in the needle stop member 52 which are too small to accommodate the syringe needle.

The location and extent of the needle stop member 52 is arranged to prevent any penetrations of the needle into a base 54 of the tissue expander 40.

A further embodiment of the tissue expander is generally indicated by the reference number 60 in FIG. 6. The tissue expander 60 comprises a closed shell 62 formed with a wall 64 that defines an expandable internal chamber 66.

The wall 64 includes a self-sealing layer or shell 68 of elastomeric material sandwiched between inner and outer layers 70 and 72 of non-flowable elastomeric material. The self-sealing layer 68 is formed of material identical to that of the layer 18 and the layers 70 and 72 are formed of material identical to that of the layer 20.

A needle stop member 74, shown in mesh form, is attached to the wall 64 in a manner similar to that described for the attachment of the needle stop member 52 to the wall 44. The mesh openings (not shown) in the needle stop member 74 permit communication between portions of the chamber 66 above and below the needle stop member 74. The mesh openings are also of small enough size to prevent penetration of the syringe needle 32. A base 76 of the tissue expander 60 is thus protected from needle penetrations.

The tissue expander 60 is used in a manner similar to that previously described for the tissue expander 10 and has no valve arrangement or entry port. However, the self-sealing layer 68, upon removal of a needle (not shown) that has penetrated the wall 64, will flow or expand into openings in the layers 70 and 72 that are caused by the needle penetration.

Still another embodiment of the tissue expander is generally indicated by the reference number 80 in FIG. 7. The tissue expander 80 comprises a closed shell 82 formed with a wall 84 that defines an expandable internal chamber 86.

The wall 84 of the tissue expander 80 is constituted by a self-sealing layer 88. The self-sealing layer 88 serves the dual purpose of establishing the confines of the tissue expander 40 and sealing any openings caused by needle penetrations during infusion or depletion of fluid from the chamber 86.

Although not shown, a needle stop member similar to any of the needle stop members previously described is included in the tissue expander 80 in a fashion similar to that described for the previously disclosed tissue expanders.

The tissue expander 80 is used in a manner similar to that previously described for the expander 10 and does not include a valve arrangement or entry port.

Still another embodiment of the tissue expander is generally indicated by the reference number 90 in FIG. 8. The tissue expander 90 comprises a closed shell 92 formed with a wall 94 that defines an expandable internal chamber 96.

The wall 94 includes a self-sealing layer or shell 98 of elastomeric material bonded to the inside of a layer or shell 100 of non-flowable elastomeric material. The self-sealing layer 98 is formed of a material identical to that of the layer 18 and the shell 100 of non-flowable elastomeric material is identical to that of the shell 20. The shell 100 incorporates a flexible mesh 102 formed of dacron. The flexible mesh 102 helps control the expansion of the chamber 96 and also enhances the self-sealing characteristics of the self-sealing layer 98.

The tissue expander 90 also incorporates a needle stop member (not shown) identical to any of the previously described needle stop members. The tissue expander 90 is used in a manner similar to that previously described for the expander 10 and does not include a valve arrangement or entry port.

Figure 9:
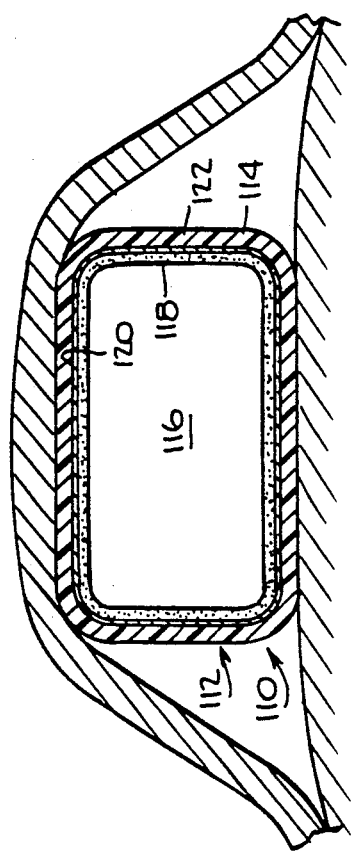

A still further embodiment of the tissue expander is generally indicated by the reference number 110 in FIG. 9. The tissue expander 110 comprises a closed shell 112 formed with a wall 114 that defines an expandable internal chamber 116.

The wall 114 includes a self-sealing layer 118 of elastomeric material that is adhesively joined with an adhesive 120 to the inside of a layer or shell 122 of non-flowable elastomeric material. The layer 118 is formed of a material identical to that of the layer 18 and the layer 122 is formed of an elastomeric material identical to that described for the layer 20.

The tissue expander 110 also includes a needle stop member (not shown) identical to any of the previously described needle stop members. Operation of the tissue expander 110 which does not include a valve arrangement or entry port is similar to that of the tissue expander 10.

Figure 10:
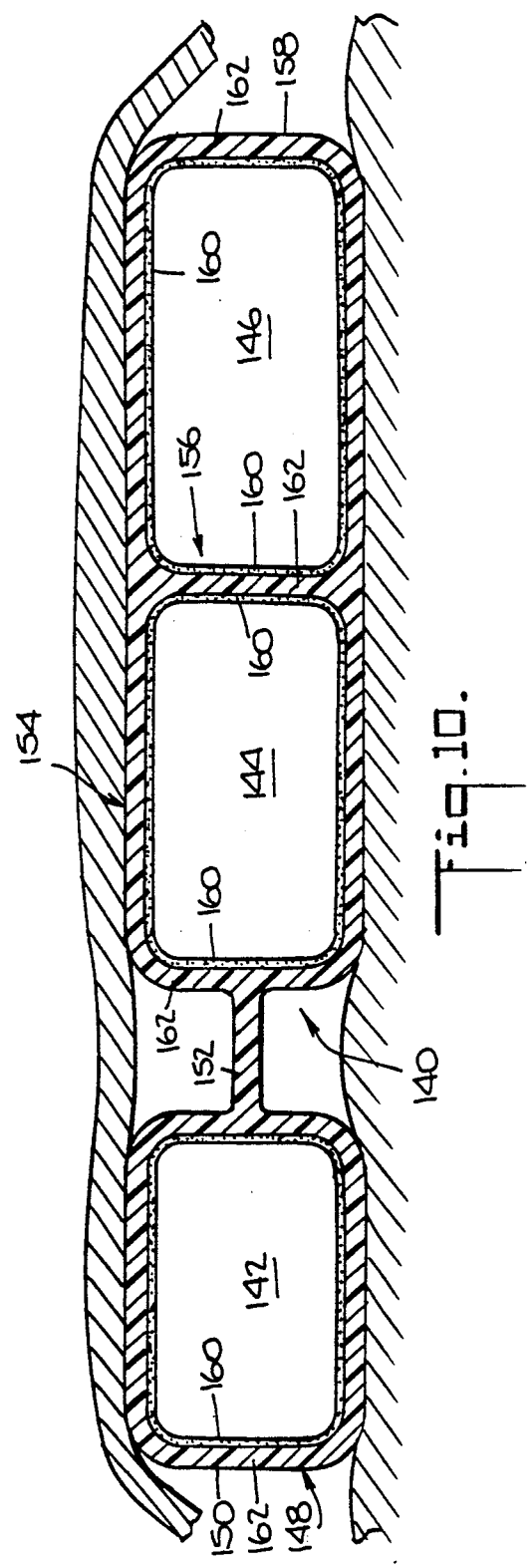

A further embodiment of the tissue expander is generally indicated by the reference number 140 in FIG. 10. The tissue expander 140 includes a plurality of noncommunicable chambers 142, 144 and 146.

A closed shell 148 formed with a wall 150 defines the chamber 142. The shell 148 is joined by a joining member 152 to a shell 154 which has a dividing wall 156 for separating the chambers 144 and 146.

Under this arrangement, the shells 148 and 154 are spaced from each other, yet joined together to constitute a single tissue expansion device. Also under this arrangement, the shell 154 has multiple chambers.

A shell wall 158 on the shell 154 and the shell wall 50 of the shell 148 include an elastomeric self-sealing layer 160 joined to the inside of a non-flowable elastomeric layer 162. The dividing wall 156 includes the non-flowable elastomeric layer 162 sandwiched between the self-sealing layers 160. The self-sealing layer 160 is formed of a material identical to the self-sealing layer 18 and the non-flowable elastomeric layer 162 is formed of a material identical to the elastomeric layer 20.

Each of the chambers 142, 144, and 146 include respective needle stop members (not shown) which are identical to any of the previously described needle stop members.

The securing or locating arrangements for the needle stop members (not shown) incorporated in each of the chambers 142, 144 and 146 are identical to any of the previously described arrangements.

It will be noted that the expansion chambers 142, 144 and 146 do not communicate with each other, do not have entry ports and do not communicate with any outside valve arrangement. Each of the chambers 142, 144 and 146 are separately infused with fluid by means of a syringe (not shown).

The self-sealing characteristics of the tissue expander 140 function in a manner similar to that previously described. The multi-chamber tissue expander arrangement of this embodiment allows selective expansion of predetermined areas of tissue, wherein the expansion is controlled by the shape and/or arrangement of the respective chambers 142, 144 and 146.

The self-sealing characteristics of the tissue expander 140 with multiple chambers provides a simplified means for expanding tissue in accordance with predetermined expansion requirements. Since none of the expansion chambers 142, 144 or 146 requires an outside valve arrangement, the surgery necessary to implant and/or remove the tissue expander 140 is relatively simple and nonextensive.

It should be noted that the wall portion of any of the embodiments of the tissue expander can be formed to provide differential expansion. Thus some portions of the wall may be thicker or thinner than other portions whereby the thin portions have greater expandability than the thick portions in accordance with an ultimate desired predetermined shape or contour of the tissue expander.

Some advantages of the present invention evident from the foregoing description include a tissue expander that does not require a separate valve arrangement to control the admission or withdrawal of fluid into an expansion chamber, and a compact, efficient tissue expander device that can be easily implanted and removed without the extensive surgery that accompanies implantation of tissue expanders with valve arrangements. A further advantage is that the tissue expander can be infused over a relatively wide area of skin, thereby minimizing the potential discomfort to a patient being subject to repeated infusions through a small discrete area of skin. The self-sealing characteristics of the tissue expander at the fluid expansion chamber permit the elimination of a valve arrangement and fluid entry port.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A valveless and portless tissue expander for implantation in a patient comprising, a closed shell defining an internal chamber, said shell being substantially collapsible when said chamber is empty and expandable upon infusion of fluid into said chamber, said shell including a shell wall formed of a needle penetrable material, self-sealing means throughout a substantial portion of said shell wall for self-sealing a needle hole formed by a needle penetrating therethrough for injecting fluid into or removing fluid from said chamber by the flowing together of shell wall material at said needle hole and, a needle impenetrable needle stop member at least party disposed within said shell chamber for stopping a needle that passes through said shell wall into said chamber from continuing to pass outwardly from said chamber.

2. The tissue expander as claimed in claim 1, wherein said shell wall comprises a layer of self-sealing elastomeric material.

3. The tissue expander as claimed in claim 1, wherein said shell wall comprises a layer of self-sealing elastomeric material joined to a layer of non-flowable elastomeric material.

4. The tissue expander as claimed in claim 3, wherein the layer of self-sealing elastomeric material is an exterior layer of said shell.

5. The tissue expander as claimed in claim 4, wherein the layer of self-sealing elastomeric material is provided over substantially the entire exterior area of said shell.

6. The tissue expander as claimed in claim 3, wherein the layer of self-sealing elastomeric material is an interior layer of said shell.

7. The tissue expander as claimed in claim 6, wherein the layer of self-sealing elastomeric material is provided over substantially the entire interior area of said shell.

8. The tissue expander as claimed in claim 1, wherein said shell wall comprises a layer of self-sealing elastomeric material sandwiched between two layers of non-flowable elastomeric material.

9. The tissue expander as claimed in claim 1, including means for stopping a needle that has penetrated said shell into said chamber from passing outwardly of said chamber.

10. The tissue expander as claimed in claim 1, wherein said shell includes a plurality of separate internal chambers.

11. The tissue expander as claimed in claim 10, wherein said internal chambers are noncommunicable with each other.

12. The tissue expander as claimed in claim 10, wherein said internal chambers are divided by a common wall portion comprising at least one layer of self-sealing elastomeric material.

13. The tissue expander as claimed in claim 1, comprising a plurality of said shells joined together such that said tissue expander includes multiple chambers.

14. The tissue expander as claimed in claim 13, wherein at least two of said shells are spaced from each other.

15. The tissue expander as claimed in claim 13, wherein at least two of said chambers are divided by a common wall.

16. The tissue expander as claimed in claim 2, wherein the self-sealing elastomeric material is selected from the group consisting of bromo butyl rubber, latex rubber, silicone gel, hydrogel, and methyl vinyl silicone.

17. The tissue expander as claimed in claim 1, wherein the needle penetrable material comprises a layer of non-flowable elastomeric material selected from the group consisting of silicone rubber, polyurethane elastomer and polyester.

18. A valveless and portless tissue expander for implantation in a patient comprising a substantially collapsible closed shell expandable to a predetermined size and shape, said shell having a shell wall with a predetermined minimum wall thickness, said shell wall being formed of a needle-penetrable elastomeric material, self-sealing means throughout a substantial portion of said shell wall for effectively self-sealing a needle hole formed by a needle penetrating therethrough for injecting fluid into or removing fluid from said chamber, and a needle impenetrable needle stop member at least partly disposed within said shell chamber for stopping a needle that passes through said shell wall into said chamber from continuing to pass outwardly from said chamber.

19. A method of expanding tissue comprising,
(a) forming a collapsible and expandable closed shell with a wall of needle-penetrable material to define an internal chamber,
(b) rendering the wall of the shell self-sealing with respect to needle penetration by use of a material that flows together at a needle opening in the wall when the needle is inserted into and withdrawn from the wall,
(c) providing the self-sealing material throughout substantially the entire area of the shell,
(d) including within said shell chamber a needle impenetrable needle stop member for stopping a needle that passes through said wall into said internal chamber from continuing to pass outwardly from said chamber,
(e) completely enclosing the chamber within the shell such that there is no entry port or valve arrangement for the shell and any introduction of fluid into the shell or removal of fluid from the shell must be accomplished by penetration of the shell wall with a needle,
(f) penetrating the wall of said shell anywhere with a needle and infusing fluid directly into said chamber or removing fluid directly from said chamber through the needle,
(g) removing the needle from the wall of said shell so as to create an opening in said shell wall, and
(h) self-sealing the opening created by the needle.

20. A method of expanding tissue comprising,
(a) forming a tissue expander having a plurality of collapsible and expandable interconnected closed shells each having a wall of needle-penetrable material defining an internal chamber,
(b) rendering the wall of each shell self-sealing with respect to needle penetration by use of a material that flows together at a needle opening in the wall when the needle is inserted into and withdrawn from the wall,
(c) providing the self-sealing material throughout substantially the entire area of each shell wall,
(d) including in each chamber a needle impenetrable needle stop member for stopping a needle that passes through a wall into a chamber from continuing to pass outwardly from said chamber,
(e) completely enclosing the chamber within each shell such that there is no entry port or valve arrangement for any shell and any introduction of fluid into any shell or removal of fluid from any shell must be accomplished by penetration of the shell wall with a needle, and
(f) penetrating the wall of a shell with a needle and infusing fluid directly into its respective chamber through the needle.

* * * * *